United States Patent [19]

Herschler

[11] 4,333,922
[45] Jun. 8, 1982

[54] METHOD FOR THE TREATMENT OF WATER-LIVING ANIMALS WITH HEALTH MODIFYING AGENTS

[76] Inventor: Robert J. Herschler, 3080 NW. 8th St., Camas, Wash. 98607

[21] Appl. No.: 657,228

[22] Filed: Feb. 11, 1976

Related U.S. Application Data

[63] Continuation-in-part of Ser. No. 505,396, Sep. 12, 1974, abandoned.

[51] Int. Cl.³ .................... A61K 39/12; A61K 31/14; A61K 31/17
[52] U.S. Cl. ........................................ 424/89; 424/88; 424/92; 424/153; 424/320; 424/322; 424/358
[58] Field of Search .................. 424/153, 320, 322; 128/1 R

[56] References Cited

U.S. PATENT DOCUMENTS 3,472,931 10/1969 Stoughton .......................... 424/320
4,009,259 2/1977 Ament et al. ......................... 424/88

OTHER PUBLICATIONS

Medveczky–Chem. Abst., vol. 66, (1967), p. 5773k.

*Primary Examiner*—Sam Rosen
*Attorney, Agent, or Firm*—Bruce G. Klaas

[57] ABSTRACT

A process is described for the introduction of health and/or welfare modifying agents, such as vaccines, to water-living animals such as fish. The health and/or welfare modifying agents are introduced into and across an epithelial membrane, such as the gill membrane, of the water-living animal by contacting the animal with the vaccine and then subjecting the animal to a negative pressure differential followed by a rapid release of the negative pressure, by contacting the epithelial membrane with a hyperosmotic concentration of a membrane permeability altering agent, either simultaneously with or prior to contacting the animal with the health and/or welfare modifying agent, or by contacting the epithelial membrane with a hyperosmotic concentration of a membrane permeability altering agent either simultaneously with or prior to contacting the animal with the health and/or welfare modifying agent followed by subjecting the animal to a negative pressure differential and then a rapid release of the negative pressure. Subjecting the animal to a negative pressure differential followed by a rapid release of the negative pressure results in a forceful infiltration of the health and/or welfare modifying agent into the body cavities of the animal. The membrane permeability altering agent renders the epithelial membrane reversibly permeable to the health and/or welfare modifying agent. Effective membrane permeability altering agents include chemical compounds having a molecular weight of about 58 to about 61, with the most preferred membrane permeability altering agents being selected from the group consisting of acetamide, urea, sodium chloride and mixtures thereof.

28 Claims, 4 Drawing Figures

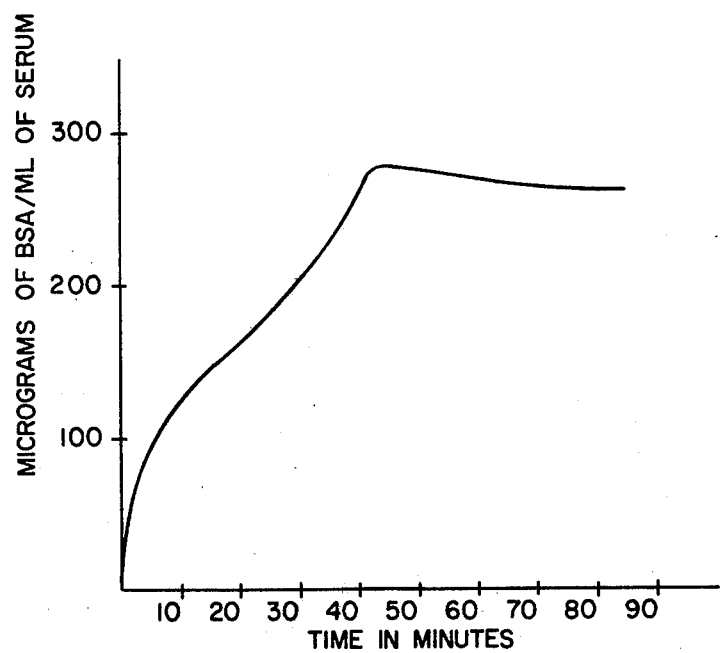
Fig _ 1
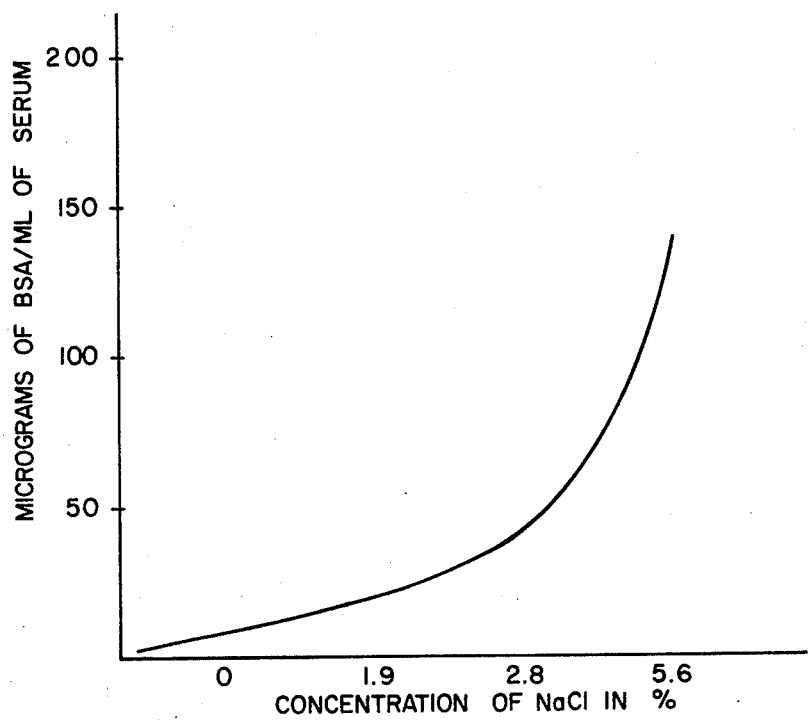
Fig _ 2

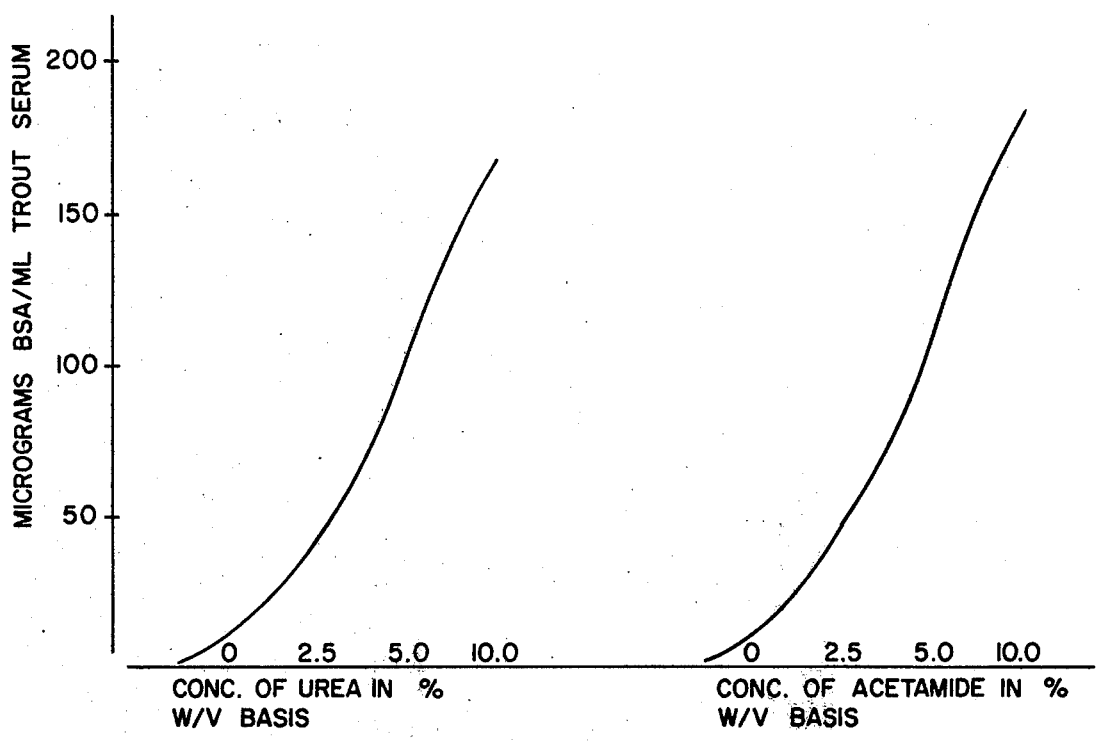
Fig_3
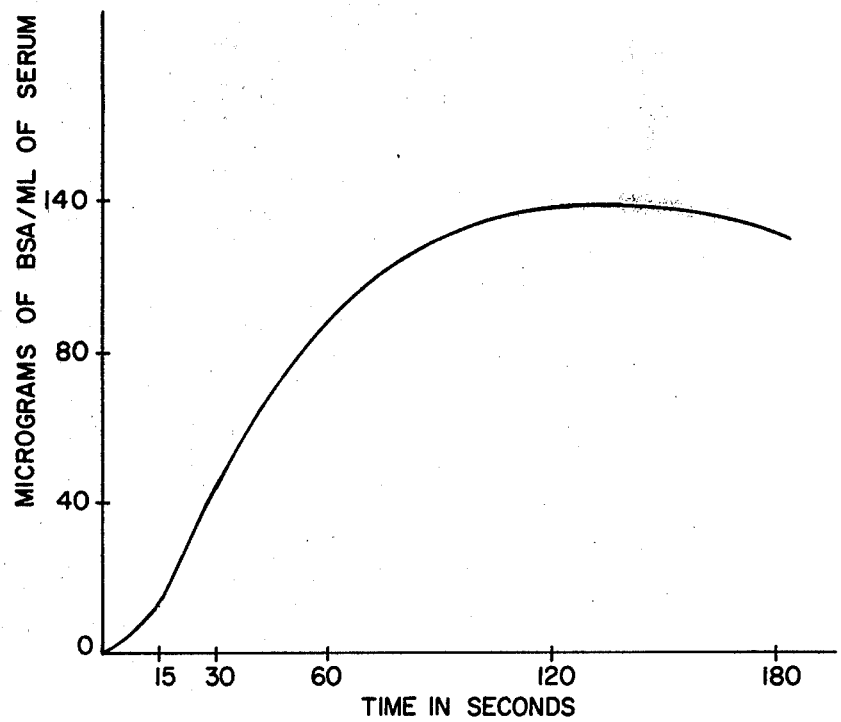
Fig_4

METHOD FOR THE TREATMENT OF WATER-LIVING ANIMALS WITH HEALTH MODIFYING AGENTS

BACKGROUND AND SUMMARY OF THE INVENTION

The present application is a continuation-in-part of U.S. patent application Ser. No. 505,396 filed Sept. 12, 1974, for VACUUM INFILTRATION AS A TREATMENT OF WATER-LIVING ANIMALS, the benefit of whose filing date is claimed herein.

The present invention relates to a process for the positive, direct, multi-avenue introduction of health and/or welfare modifying agents to water-living animals as exemplified by, but not limited to, fish. More especially, the present invention relates to the introduction of health benefiting agents such as vaccines to water-living animals. The resultant effect of the described process following and simultaneous to the infiltration of the agent is deep biomembrane penetration, systemic assimilation, and body fluid circulation by the water-living animal.

The vaccination of higher, terrestrial vertebrates is a relatively simple matter. One can administer a vaccine, a bacterin, or other health and/or welfare modifying product by needle and hypodermic injection, by air gun, and sometimes by the oral route with specific vaccines supported in a water soluble carrier (analogous to a sugar cube used with oral polio). This allows for solution vaccine contact at the mucous membrane of the buccal cavity, i.e., before entry and inactivation by the stomach.

The vaccination of water-living animals such as fish is a far more difficult problem. If it is desired to needle or air-jet inject a fish, the following problems arise:

1. One must locate and catch the fish.
2. It is necessary to firmly hold a protective mucous covered, streamlined and wriggling active individual.
3. Penetration must be made of a scale covered surface and into a nonvital mass of tissue (i.e., muscle). This step alone is a very difficult task because to be most effective, it must be done with small fish ranging from one inch in size to six inches and with perhaps 100–1000 fish per pound. Many fish diseases only are serious problems when the fish are at the one inch to three inch size; that is, at a very juvenile stage. Therefore, the small fish need the protective vaccine or other therapeutant when they are most vulnerable and most difficult to handle.
4. A high death rate will occur after the trauma of needle or air jet vaccination. Fish are trauma prone and often will die if merely handled roughly. With fish, injection procedures historically demonstrate poor survival.
5. High labor costs. A team of 4–6 persons is a minimum for this operation and they will normally vaccinate only 8000–10000 fish in an eight hour work shift, assuming everything goes smoothly. A usual salmon hatchery, as an example, holds between 10 to 20 million fish, all requiring protective vaccinations in a brief 2 to 3 week period. A very productive vaccination line therefore can only service about 1 million fish in about 33 shifts. A total of about 660 vaccination team shifts are required for just one large hatchery. The economics of this type of operation are not favorable. Perhaps $40/day×6 workers×660 shifts=$158,400 or roughly ¾ cent/fish. Excluded in this single calculation are the cost of vaccination, materials and equipment. Hatcheries cannot afford such costs, even if the needle injection method were feasible and effective from a fish survival standpoint. If the value of the fish killed thereby is added in, then the cost of the needle injection method becomes significantly higher.

Because of the problems with injection procedures, the oral route has been more extensively tested. Here particularly, the water environment works against the process. For a successful vaccination process with the limited number of diseases where oral administration is theoretically feasible, it is not possible to use a water soluble "sugar-cube like" vaccine support. Such supports obviously would dissolve and dissipate the vaccine before adequate fish membrane contact. Therefore, water insoluble baits with incorporated vaccine have been used of necessity. However, little, if any, of the essential buccal cavity mucous membrane contact with the vaccine is possible. Fish in hatcheries usually go into a feeding frenzy when given fish pellets or bait. Thus, the vaccine yet in the bait or feed pellet is ingested whole. On passage to the stomach, the vaccine antigenic component(s) are rapidly inactivated by the gastric pH and digestive enzymes, and likely systemic assimilation is poor through the gut wall in any case.

To overcome the difficulties inherent in prior delivery systems for other organisms, it has been previously proposed to introduce health modifying agents into and across an external membrane of a human or animal subject by concurrently or sequentially contacting the membrane with a sufficient amount of dimethyl sulfoxide (DMOS) to enhance penetration of the health modifying agent across the membrane. For example, U.S. Pat. Nos. 3,551,554, 3,711,602, and 3,743,727 relate to such processes. While DMSO appears to be highly effective in enhancing the permeability of epithelial membranes of humans and mammalian animals, it appears to be somewhat less effective on attempted delivery to gilled animals. The gill membrane, yet poorly defined and understood, appears to present a different kind of membrane structure. Furthermore, DMSO loses its effectiveness as a membrane penetrant in a predominantly water based system, where it effects a considerable organization with the water molecules and thereby reduces its transmembrane carrier properties.

At the present time, the mortality rate due to disease in fish is high. The loss of fish involves not thousands of dollars, but hundreds of millions of dollars, in just the Alaska sockeye run, or the Frazer river run, or the Columbia river run, or the Sacramento river run. The present invention provides a method for the protection, service to and salvage of a multibillion dollar industry; and also aids in providing good protein to a world where maintenance of the food supply is becoming an ever increasing problem.

The present invention provides a new process for the systemic introduction of health and/or welfare altering agents through an epithelial membrane, such as the gill membrane, of the water-living animal. The health and/or welfare modifying agents may be introduced into the animal by contacting the animal with the agent and imposing upon the animal a measurable negative pressure (vaccum) which at least partially collapses gas-filled sinuses and other structures and body cavities, degasses body fluids and support organs, and results in a compressed elastic, gas decreased animal. Thereafter, the animal is next decompressed through a sharp or rapid return to ambient pressures accompanied by a rapid filling of degassed organs, tissues, body cavities and body fluids with the health modifying agent in contact with the animal body. The health modifying agents may also be introduced into the animal by contacting the epithelial membrane with a hyperosmotic concentration of a membrane permeability altering agent either simultaneously with or prior to contacting the animal with the health modifying agent, or by contacting the epithelial membrane with the health modifying agent and a hyperosmotic concentration of a membrane permeability altering agent followed by subjecting the animal to a negative pressure differential and then a rapid release of the negative pressure.

BRIEF DESCRIPTION OF THE DRAWING

Referring now to the accompanying drawing:

FIG. 1 is a graph showing the uptake by rainbow trout of bovine serum albumin, (BSA) from an aqueous solution containing 2% by weight BSA and 5.3% by weight NaCl, as a function of time.

FIG. 2 is a graph showing the uptake by rainbow trout of BSA from an aqueous solution containing 2% by weight BSA and NaCl, as a function of NaCl concentration.

FIG. 3 is a graph showing the uptake by rainbow trout of BSA from an aqueous solution containing 4% by weight BSA and urea or acetamide, as a function of urea or acetamide concentration.

FIG. 4 is a graph showing the uptake by rainbow trout of BSA from a 2% by weight BSA solution, following a previous pretreatment of the trout in a 5.3% by weight aqueous NaCl solution, as a function of time.

DETAILED DESCRIPTION OF THE INVENTION

According to the inventive concepts, water-living animals, such as fish, shellfish and crustaceans, are treated by introducing health and/or welfare modifying agents through an epithelial membrane, such as the gill membrane, of the animal.

As used herein, the expressions "health and/or welfare modifying agent" and "health modifying agent" are intended to encompass vaccines, pharmaceuticals and/or nutritional supplements which are primarily related to the health of the animal, such as antigens, antimicrobials, antiparasitics, antihistamics, neuropharmacologics, anti-inflammatories, anticoagulents, vasodialators, U.V. screening agents, antibiotics, nutrients, vitamins, toxicants, insecticides and minerals. Specific examples include: sulfamerazine, sulfamethoxazole, nifurpirinol, erythromycin, furazolidone, 2-amino-5 nitrothiazole, tetracycline, antibiotics, thiabendazole, *Aeromonas salmonicida* antigen preparation, *Vibriosis anguillarum* antigen preparation, Infectious hematopoietic necrosis antigen preparation, Infectious pancreatic necrosis antigen preparation, *Aeromonas liquefaciens* antigen preparation, Hagerman enteric red mouth antigen preparation, *Vibrosis parahaemolyticus* antigen preparation, ascorbic acid and sodium salt, terramycin, nitrofurantoin trypaflavine, atebrine, chloromycetin, dylox kanamycin, malachite green and ferric sulfate. They are also intended to encompass welfare/protective agents such as odor and taste repellants as to ward off potential predators, dyes to effect a marking system of a crab or fish, flavorants, or for other diverse commercial purposes.

The present invention is concerned with the delivery of fish vaccines and bacterins to fish and especially with respect to the treatment of endangered species of fish.

Other cold blooded water-living animals, such as shellfish and crustaceans, may also be treated in accordance with this invention. In the more detailed aspects of the invention, vaccination is conducted with dispersed or dissolved or emulsified biologicals in a water medium with water-living animals in intimate contact therein.

The health and/or welfare modifying agent may be introduced into the water-living animal by imposing a negative pressure differential on the water-living animal body for a sufficient period of time to expel the gas contained in the animal body and effect a substantial vaccum in the body structure and cavities of the animal. This is carried out while the animal is in contact with the health and/or welfare modifying agent. Naturally, the susceptibility to injury of various fish by subjecting to vacuum or substantial negative pressure will differ and the negative pressure that is selected will be based on tests so that no overt injury is sustained by the fish or other water-living animals.

Then the negative pressure is quickly relieved to bring the pressure on the animal back up to at least normal ambient pressure. The rapid decompression results in acceptance by forced infiltration of the agent in contact with the animal body into a plurality or multiplicity of locations on the animal body.

The health and/or welfare modifying agent may be employed in the form of a liquid emulsion, aqueous solution or dispersion. Mixtures of active ingredients may be used. The vaccine may comprise an antibiotic, tranquilizer, stabilizer, emulsifier, surface active agent and the like.

The negative pressure (vacuum) and the vacuum release can be imposed on the animal in any convenient holding vessel wherein animals, e.g., fish, are both confined and totally immersed or covered by or at least totally wetted in a fluid of vaccine content. Water is most common as the medium but other life support solvents, such as a Freon, which various animals tolerate for reasonable times, may also be used. Freon is a trademark for a variety of polyfluorinated hydrocarbons as is known in the art.

The process of expressing air and other dissolved or entrained gases from the fish leaves a multitude of elastic voids at vacuum state. Thereafter, sharply breaking the vacuum causes a rapid return to normal pressure whereby the degassed elastic voids, gas deficient body fluids, etc., are required to accept the vaccine fluid as the gas replacement. The period of negative pressure exposure can vary considerably, for example, 1 to 5 minutes. The preferred time is 2 to 3 minutes. The process can be repeated in a series of successive vacuum-vacuum break cycles where necessary to deliver desired vaccine dosages to the fish.

This described system has been repeatedly tested with gold fish, trout and two species of salmon. It is seen that fish give up a surprising amount of gas under moderate vacuum and survive without post-treatment stress deaths or even mild untoward effects.

Species of fish vary markedly in vacuum tolerance and many will withstand a gauge pressure drop from 30 inches Hg (indicating ambient normal pressure) to 18 inches Hg (indicating negative pressure). Some species indicate greater vacuum tolerance down to 4 or 5 inches of Hg. Vacuum limits are imposed depending on the species of animal and may be applied without subsequent serious undesired untoward effects. Preferably, the process is practiced where the vacuum applied is at least a drop of from 30 inches of Hg pressure (ambient pressure) to at least 25 inches of Hg pressure and yet less than a drop to a gauge reading of 5 inches of Hg.

The vacuum containment vessel may be constructed to hold porous basket-like holders or transfer trays (units) for water-living animals to assure that manual handling is expedited and minimized. Suitably, the entire construction can be manufactured from non-toxic plastics, metals and alloys exemplified by aluminum, stainless steel, polyacrylates, polyolefins, polyvinyl chloride polymers, epoxies and/or polyesters.

It may be desired for the vacuum containment vessel holding fluids to have controls in order to regulate the temperature of the holding fluids to closely match the current temperature of the subject water-living animals being infiltrated, as water-living organisms poorly tolerate sharp temperature changes even without other stress factors. Suitably, the temperature will range from 5° to 15° C. for contact with the agent. This can be followed by treatment at slightly higher temperature, for example, 15°–20° C. for a period of time to permit the agent to react with the animal.

Generally, the process is carried out where the vacuum containment vessel with holding health/welfare fluid under regulated temperature receives fish to a capacity not exceeding the fluid immersing or total body wetting capacity. This is followed by application of negative pressure to a gauge reading of 30 inches less 10 inches Hg (20 inches Hg total pressure) for a holding time of 2 minutes, thence the vacuum is rapidly relieved. This may be followed by successive cycles to achieve desired dosage levels and then by rapid transfer of the vacuum infiltration vaccinated fish to their normal containment.

Certain aspects of the invention involve discovery of a correlation between membrane permeability and hyperosmotic solute molecular weight characteristics. The water-living animals may be treated by introducing the health modifying agent through an epithelial membrane, such as a gill membrane, of the animal when the membrane has been rendered reversibly permeable to the health modifying agent by contacting the membrane with an effective amount of a membrane permeability altering agent having a molecular weight in the range of about 58.0 to about 61.0.

Suitable membrane permeability altering agents include aqueous solutions of water soluble chemicals having a molecular weight in the range of about 58.0 to about 61.0 and having a lesser binding affinity for water than dimethyl sulfoxide. The suitability of various membrane permeability altering agents in the practice of these concepts is dependent not only upon their membrane permeability altering properties, but also on environmental factors, such as toxicity to the water-living animals, plant life, land animals, etc. Thus, while certain compounds, e.g. acetaldoxime, acetone, allyl alcohol, propanol, isopropanol, ethylene diamine, ethylene glycol, and ethylene sulfide, etc., may have acceptable molecular weights and membrane permeability altering properties, they may be too environmentally toxic to be useful in practice. Such toxicities should be readily apparent from the art. Particularly preferred membrane permeability altering agents, which have been found to exhibit no toxicity or relatively low levels of toxicity, as used herein, include aqueous solutions of acetamide, urea, sodium chloride and mixtures thereof. It has been determined that the following water-living plants and animals of both the fresh and marine environments can be safely challenged with hyperosmotic concentrations of urea, acetamide and NaCl: *Aerobacter aerogenes* (bacteria); *Escherichia coli* (bacteria); Saccharomyces (yeast); Chlorella (algae); Euglena (protozoan); Cabomba (fanwort plant); Elodea (anacharis plant); Lemna minor (duckweed plant); Vallisneria (eel grass plant); Philodina (rotifer); *Dugesia tigrina* (brown planaria); Daphnia (arthropod); Dragonfly nymph (insect); Mosquito larva (insect); Pond snail (mollusk); Rana tadpole (amphibian); *Salmo gairdneri* (rainbow trout); *Oncorhynchus kisutch* (coho salmon); *Onchorhynchus tshawytscha* (chinook salmon); Ulva (marine plant); Fucus (marine plant); *Hedophyllum sessile* (marine plant); Odonthalia (marine plant); *Prionitis andersoni* (marine plant); *Rhodomela larix* (marine plant); Crayfish (anthropod); *Zostera marina* (marine eel grass plant); Collisella (limpet); Notoacmeae (limpet); *Mytilus californiaus* (mussel); *Thais emerginata* (purple snail); Oyster larvae; *Tegula emerginata* (purple snail); Oyster larvae; *Tegula funevralis* (black turban snail); *Strongylocentrotus purpuratus* (purple sea urchin); Brine shrimp (sanders); *Petrolisthes cinctipes* (porcelain crab); and *Hemigrapsus nudus* (purple shore crab.)

The membrane permeability altering agents are effective to render the membrane reversibly permeable to the passage of health modifying agents therethrough when they are present in the aqueous solution in hyperosmotic concentration, more preferably about 2 to about 20 times isomotic concentration and most preferably about 3 to about 10 times isosmotic concentration. Isosmotic concentrations of the preferred membrane permeability altering agents for most water-living animals are: acetamide—about 1.2 g/100 ml, urea—about 1.7 g/100 ml and NaCl—about 0.9 g/100 ml. Selection of the most desired concentration levels depends on many factors including the type and stability of the health modifying agent, environmental water temperature, environmental water hardness, environmental water salinity, treatment time, animal species and age. The epithelial membrane of the water-living animal is contacted with an aqueous solution of the membrane permeability altering agent, as for example, by bathing or immersing the animal in the aqueous solution of the membrane permeability agent or by applying the aqueous solution of the membrane permeability altering agent directly to the membrane while the animal is either totally or partially out of water. The membrane may be contacted with the membrane permeability altering agent simultaneously with or prior to contacting the animal with the health modifying agents, and/or simultaneously with or prior to one or more vacuum-vacuum break cycles as previously described. The aqueous solution of the membrane permeability altering agent may optionally be purified prior to applying the solution to the membrane, for example, by passing the aqueous solution through a bed of activated charcoal to remove ammonia, polyvalent cations and other compounds which are harmful to the water-living animals.

In the practice of these concepts, an epithelial membrane, such as the gill membrane, of a water-living animal is exposed to a hyperosmotic concentration of the membrane permeability altering agent for a sufficient period of time to render the membrane permeable, or open, to the passage of the health modifying agent into the animal. Effective exposure times will vary depending on the nature of the animal to be treated and other conditions, but will generally be on the order of about 1 to about 30 minutes, more preferably about 2 to about 20 minutes and most preferably about 3 to about 10 minutes. Exposure to the membrane permeability altering agent causes the membrane to become "reversely permeable" to the desired health modifying agent. In other words, the membrane becomes open or permeable for a limited period of time and then it gradually becomes less permeable, finally returning to its normal state.

Either simultaneously with or subsequent to contacting the epithelial membrane with the membrane permeability altering agent, the membrane is similarly contacted with the health modifying agent. The health modifying agent is administered to the membrane either as an aqueous solution or dispersion, as, for example, by bathing or immersing the membrane in the aqueous solution or dispersion, or by contacting the membrane with the health modifying agent while the animal is either partially or totally out of water. Effective concentrations of the health modifying agent in the aqueous solution or dispersion are dependent upon the particular health modifying agent employed and the desired biological effect to be achieved. When the health modifying agent is administered to the membrane subsequent to the treatment of the membrane with the membrane permeability altering agent, an effective exposure time to the health modifying agent is about 0.5 to about 15 minutes, more preferably about 1 to 10 minutes and most preferably about 2 to about 5 minutes. It has been determined that a relatively high viscosity in the aqueous solution or dispersion of the health modifying agent has an inhibiting effect on uptake of the health modifying agent by the water-living animal. It is therefore preferable to apply the health modifying agent to the membrane in an aqueous solution or dispersion having a viscosity less than about 10cp. and more preferably in a solution or dispersion having a viscosity as close to 1cp. as is possible.

In cases where the health modifying agent and the membrane permeability altering agent are compatible, the membrane may be contacted with the membrane permeability altering agent either simultaneously with or prior to contacting the membrane with the health modifying agent. In some cases, however, the health modifying agent will not be compatible with the membrane permeability altering agent, thereby necessitating a "pretreatment" of the membrane with the membrane permeability altering agent followed by a treatment with the health modifying agent before the membrane reverses to its normal, relatively non-permeable condition.

It has also been found that the health modifying agent uptake by water-living animals can be further enhanced by incorporating about 1 to about 200, more preferably about 3 to about 150 and most preferably about 5 to about 125 ppm of a poikilothermic vertebrate vasodilator, such as 2- (thiazolyl) benzimidole, into the aqueous solution of the membrane permeability altering agent. The 2-(4-thiazolyl) benzimidole is a medicinal fungicide which incudes hyperrespiration in and has a tranquilizing effect on water-living animals thereby enhancing transmembrane passage of the health modifying agent.

Introduction of the health modifying agent across the epithelial membrane of the water-living animal may be achieved by contacting the membrane with a hyperosmotic concentration of a membrane permeability altering agent either simultaneously with or prior to contacting the animal with the health altering agent followed by subjecting the animal to a negative pressure differential and then a rapid release of the negative pressure, as previously described. The combined effect of the membrane permeability altering agent coupled with negative pressure and negative pressure break greatly enhances transmembrane passage of the health modifying agent.

The following examples are illustrative of the enhancement of health modifying agent penetration into and across the epithelial membrane of water-living animals. Unless otherwise specified, all percentages are based on weight.

EXAMPLE I

Testing nos. 1–7 studied the effect of a two minute immersion (silver salmon, *Oncorhynchus kisutch*) in 10% chemical concentration challenges (20 g chemical in 180 g water). Each testing is a 2×2 replicate or 4 fish using the same challenge solution. Total estimate period of potential "handling trauma" comprehends 0.5 minutes to solution, 2.0 minutes at vacuum in test solution, and 0.5 minutes from solution and into holding tray—circa 3 minutes total.

This testing measures both a high chemical concentrations lethality effect, and the plausibility of a static hypertonic pressure system (roughly 3×isosmolar) to force active vaccine components across membranes as it is associated with vacuum. All chemicals tested are potential vaccine vehicles having been earlier tested as safe (24 hour) at 1% w/w using rainbow trout. Only one chemical requires special discussion. This is a 2,2′,2″-nitrilotriethanol or triethanolamine, which has strong interest: (1) as the KOH replacement base to neutralize Carbopol 934; (2) for the enhancement of cationic charge potential to any vaccine; (3) as a synergist with other specific membrane active agents which decrease in vivo membrane stability.

TABLE I
STATIC IMMERSION TESTING RESULTS

| Test | Chemical | Conc w/w | Lethality at 3–4 hrs. | Lethality at 24 hrs. |
|---|---|---|---|---|
| 1 | Dimethylsulfoxide (DMSO) | 10% | none | none |
| 2 | Glycerin | 10% | none | none |
| 3 | Acetamide | 10% | none | none |
| 4 | Ethylene Glycol | 10% | none | none |
| 5 | Triethanolamine | 10% | none | 4 of 4 dead |
| 6 | Dimethylformamide | 10% | 1 of 4 distress | 2 of 4 dead |
| 7 | DMSO2 (Dimethyl sulfone) | 10% | none | none |

NOTE:
All surviving fish at 24 hours observation were frisky; apparently health therefore returned to holding pond at the hatchery. It should be further noted that chemical 5 triethanolamine on retest at 1% w/w produced no lethalities at 24 hours.

EXAMPLE II

With Testing Nos. 8–14, the vacuum infiltration procedure was used. Here a polyacrylic plastic vacuum dessicator was used along with a large crystallizing dish holding 1 liter of test solution. The challenge chemical concentration was 1% w/w basis, and the chemicals of Test 1–7 were re-evaluated under these conditions. Vacuum was drawn using a water aspirator set-up with vacuum applied for exactly two minutes. The water was of good pressure and was cold. Hence, a good vacuum developed which produced bubbles from the fish buccal and anal cavities and from the general fish surface. After two minutes, the vacuum was broken, the treated fish immediately transferred to flowing spring water in numbered holding trays, and observed for lethality and other less adverse toxicity implications. Additionally, three controls were run using only spring water as challenge to determine if the mechanical infiltration alone might induce overt stress and toxicity.

TABLE II

VACUUM INFILTRATION TESTING RESULTS

| Test | Chemical | Conc w/w | Vac. Min. | Lethality at 3-4 hrs. | 24 hrs. |
|---|---|---|---|---|---|
| 8 | DMSO | 1% | 2 | none | none |
| 9 | Glycerin | 1% | 2 | none | none |
| 10 | Acetamide | 1% | 2 | none | none |
| 11 | Ethylene Glycol | 1% | 2 | none | none |
| 12 | Triethanolamine | 1% | 2 | none | none |
| 13 | Dimethyl Formamide | 1% | 2 | none | none |
| 14 | Dimethyl Sulfone | 1% | 2 | none | none |
| 21 | none (control) | — | 1 | none | none |
| 22 | none (control) | — | 2 | none | none |
| 23 | none (control) | — | 5 | none | none |

NOTE:
All fish 2 × 2 or 4 total, each testing survived the above challenges without lethality or obvious toxicity symptoms. All were returned in frisky condition to rearing hatchery pond.

EXAMPLE III

In Tests Nos. 15-18, 2×2 replicates of fish were subjected to a simulated vaccine formulation, without any antigenic components. In this simulated vaccine, the following components were combined and the purpose for each component is cited in the following discussion. Both static and vacuum infiltration deliveries were tested with each component and the combination.

Composition—Simulated Vaccine Concentrate:

30 mg. thiabendazole (TBZ), as a 1 ml of 3% w/w presolubilized in DMSO. TBZ specifically used as an antitrauma tranquilizer, but particularly to increase gill respiration inducing greater gill membrane contact with the associated active borne vaccine components.

50 mg. oxytetracycline (Terramycin), as a 1 ml unit of the commercial injection form used here as the primary prophylaxis against secondary infections following the handling and trauma of vaccination. This broad spectrum antibiotic was selected as it is now cleared by FDA for food fish.

0.1 g Carbopol 934, a carboxyvinyl polymer used to stabilize and disperse vaccine components.

0.1 g DEAE dextran, a polycation polymer primarily used because its cationic nature provides increased attraction to the passive transport membranes which must be breached by the antigen-adjuvant combination for antibody production.

0.1 g Tween 80, used solely for surfactancy, i.e., lower liquid phase surface tension with resultant enhanced wetting.

The above components as a mull were then brought to a total volume of 20 ml with 99%+DMSO. This produced a somewhat cloudy solution. DMSO, of course, is herein used primarily to effect proper subunitizing of the killed virus into more highly effective antigenic fractions. Though movement across membranes, particularly the gill membranes with fish, is induced by hyperosmotic pressure and more particularly by a relatively sharp atmospheric pressure drop (vacuum) following which the vacuum is broken sharply causing a sharp increase to ambient atmosphere (i.e., vacuum infiltration), the fact remains that DMSO is a specific membrane-active agent which decreases membrane stability.

In Test No. 15, all four fish, 2×2 challenges were simply allowed to swim in 980 ml of spring water to which 20 ml of simulated vaccine concentrate was added. Contact time was 2 minutes. All fish survived at 24 hours, appeared frisky, and were returned to holding tanks.

In Test No. 16, four fish, 2×2 challenge were subject to the solution of No. 15 by 2 minutes vacuum infiltration. All fish survived as in Test No. 15. The one difference being that in Test No. 16, the fish were obviously tranquilized presumably by the TBZ.

In Test No. 17, again a 2×2 (4 total fish challenge), and the solution of No. 15 was used again as a static challenge, but 1 ml of 0.5% w/w basis 2,4-dinitrophenol was additionally added from a 50/50, DMSO/water solution, (DNP added is 5.0 mg/l). With first a static Test No. 17 as per Test No. 15, all four fish survived and 24 hour post were in apparent excellent condition; thus were returned to the rearing pond.

In Test No. 18, again the preceding solution of No. 17 was used but with vacuum infiltration. All fish again survived well through 24 hours observation, and were returned to the rearing pond. Again, as with Test No. 16, these vacuum infiltrated fish demonstrated pronounced tranquilization upon removal from the challenge water, an effect not seen in static Test No. 17.

EXAMPLE IV

Vibriosis in fish, caused by *Vibrio anguillarum,* is a serious disease of anadromus salmonids. Protection is possible with injected antigen or oral feedings of antigen-bearing killed organisms. However, with the later route of administration, there is no resultant circulating or humoral antibody seen and protection is marginal at best. In multiple field tests, oral feedings of any known fish vaccine has been seen to provide poor to negative protection.

A formaldehyde killed culture of *Vibrio anguillarum,* yet in the culture medium was used to vaccinate juvenile coho salmon employing only vacuum infiltration for delivery. In the vaccination process, fish of approx. 2" length were immersed in the above vaccine fluid held in a vacuum chamber. A vacuum of 15 inches Hg was produced and rapidly broken with return to ambient. This cycle was repeated 3 times, the fish removed and held in rearing ponds for 45 days. At that time humoral antibodies were detectable in the blood of treated fish and these fish demonstrated protection against a high titer virulent challenge which was rapidly lethal to the treatment control fish.

EXAMPLE V

Rhodamine B dye, tetraethylrhodamine, has a relatively large molecular weight (479) and posses reactive groups of a cationic nature. It is therefore representative of many health modifying agents, as herein defined. The effect on the systemic uptake of a 0.5% aqueous Rhodamine B dye solution by *Carassius auratus* (goldfish) after an exposure time of 10 minutes in the presence of varying membrane permeability altering agents is shown in Table III. The systemic uptake rating is based on a scale of 0 to 4, with 0 indicating no systemic uptake and 4 indicating maximum systemic uptake. Judgment of systemic uptake was based on the color of autopsy muscle in day and U.V. light, and on the color of glass fiber filtered tissue extracts using 10 ml volumes of ethanol and 1 g. of muscle tissue. Spring water at 15° C. was used in all tests.

TABLE III

Systemic Uptake of Rhodamine B Dye by Goldfish

| Test | Membrane Permeability Altering Agent | Systemic Uptake Rating |
| --- | --- | --- |
| 1 | None, pure water | 0 |
| 2 | DMSO, 10g/100ml | 2 |
| 3 | Acetamide, 10g/100ml | 3.5 |
| 4 | Urea, 10g/100ml | 3.5 |
| 5 | NaCl, 10g/100ml | 1 (fish died) |
| 6 | Acetamide/NaCl mol:mol 10g/100ml | 4 |
| 7 | Urea/NaCl mol:2 mol 10g/100ml | 4 |
| 8 | NaCl, 5g/100ml | 2 |
| 9 | Urea, 10g/100ml as 10 min. presoak followed by 5 min. in aqueous 0.5% dye | 4 |
| 10 | 5 min. in 0.5% aqueous dye, followed by urea, 10g/100ml post soak of 10 min. | 2 |

The results in Table III demonstrate that both acetamide and urea facilitate a greater degree of systemic uptake of the dye than does DMSO at the same weight/volume concentration levels and that a mixture of acetamide or urea with sodium chloride facilitates an even greater degree of uptake of the dye. As shown in Test 10, relatively low levels of dye uptake resulted from topical application of the dye followed by topical application of the membrane permeability altering agent urea.

EXAMPLE VI

The response of *Carassius auratus* (goldfish) to 2-(4-thiazolyl) benzimidazole, can be embodied in a response rating which collates time and composite animal response. In this example, 1 ml of 3% solution strength 2-(4-thiazolyl) benzimidazole diluted to 300 ml in 15° C. spring water was topically applied to *Carassius auratus* in a containment vessel for a period of 10 minutes in the presence of various membrane permeability altering agents. The effectiveness of the membrane permeability altering agents in enhancing the onset of hyperrespiration and tranquilization in the fish is represented by the response rating in Table IV. A rating of 1 indicates a minimum response while a rating of 4 indicates a maximum response in the fish.

TABLE IV

Membrane Permeability Altering Agent Effect on Benzimidazole Response in Goldfish

| Test | Membrane Permeability Altering Agent | Response Rating |
| --- | --- | --- |
| 1 | None - water only | 1 |
| 2 | DMSO, 30g/300ml | 2 |
| 3 | NaCl, 15g/300ml | 2 |
| 4 | Urea, 30g/300ml | 3 |
| 5 | Acetamide, 30g/300ml | 3½ |
| 6 | Acetamide/NaCl, mol:mol 30g/300ml | 4 |
| 7 | Urea/NaCl, mol:2 mol, 30g/300ml | 4 |
| 8 | NaCl, 15g/300ml as 10 min. presoak, then immersed in soln. of Test 1 | 2 |
| 9 | Urea, 30g/300ml as 10 min. presoak, followed with Test 1 soln. immersion | 4 |
| 10 | Acetamide, 30g/300ml as 10 min. presoak, followed with Test 1 soln. immersion | 4 |
| 11 | Test 1 soln. immersion followed with urea, 30g/300ml | 1 |

Again, urea and acetamide facilitate a higher response rating than does DMSO, indicating a higher degree of benzimidazole uptake by the goldfish. Urea and acetamide when administered as a presoak result in a particularly high response rating. When sodium chloride is coupled with either urea or acetamide, a particularly high response rating is obtained. As would be expected a reverse of Test 9, as shown in Test 11, that is immersion in the aqueous benzimidazole solution of Test 1 for 10 minutes followed by immersion in the membrane permeability altering agent of Test 9 demonstrated no measurable response enhancement over Test 1 alone.

EXAMPLE VII

The effectiveness of an immunogenic agent is generally best measured by the biological response (antibody production) ellicited when the agent is systemically introduced into test animals. A model agent or standard which provides the desired antigen-antibody response, bovine serum albumin, (BSA) has a molecular weight of about 68,000. This protein is much studied by immunologists and can be considered to be a "standard" antigen though providing no protection against any disease. In evaluating the effectiveness in vivo of the inventive concepts, BSA was hyperosmotically forced into fish, mainly through the gill organ, and separated out from the fish's blood serum using immuno-electrophoresis. if antibody-antigen complexes are measured by this system, an effective dosage of antigen has been introduced. Similar results will be seen with a disease protecting antigen. The technique depends on the movement of test antigen (using fish serum in these studies) through a gel medium and into contacting gel containing a known concentration of antiserum specific for the test antigen. The moving force is a flow of direct current. The charged, mobil antigen during movement forms a precipitate of antigen/antibody complex whose peak height and area is concentration and time dependent. To facilitate viewing the precipitation peaks, the complex was stained with Coomassie Blue followed by a destain to achieve maximum resolution.

The immunoelectrophoresis precipitation test procedure used Vernol buffer with Agarose gel coatings on 25 cm$^2$ glass slides. The specific antiserum was rabbit hyperimmune of greater than 10,000 titer. The antigen standard was BSA at 500 ppm, in rainbow trout serum. An LKB, type 3290B electrophoresis unit was employed in all tests. The destain, and solvent for stain comprised 45 parts of 95% ethanol, 45 parts demineralized water, and 10 parts glacial acetic acid.

A quantitative estimate of antigenic factor in serum assays was determined by projecting the finished slides with dye emphasized migration peaks onto a paper background. The areas under the peaks were outlined, cut out, weighed and then compared against a standard.

In this example, the average serum levels of BSA in the blood of rainbow trout was measured after the fish were immersed in an aqueous solution containing 5.3% by weight sodium chloride and 2.0% by weight of BSA. The fish, after treatment were allowed to freely swim in holding tank water and were sacrificed at the specified times. Caudal vein blood was taken from the fish using Heparinized tubes and serum was removed from the blood for assay. As shown in FIG. 1, peak blood level of BSA was reached in less than one hour after administration of the BSA to the fish.

EXAMPLE VIII

The procedure of Example VII was followed, but by running a standardized time comparison with BSA at the 2% level and with varying concentrations of sodium chloride. The rainbow trout were immersed in an aqueous solution containing BSA and NaCl for a period of 3 minutes and were then sacrificed. As shown in FIG. 2, NaCl at the 1.9% level enhanced BSA uptake by the fish over a control sample containing no NaCl. When NaCl was present at the 2.8% level, BSA uptake was even greater. The greatest amount of BSA uptake occurred with NaCl present at the 5.6% level (about 6.1 times isotonic strength).

EXAMPLE IX

The procedure of Example VIII was followed, but by running a standardized time comparison with BSA at the 4% level and with varying concentrations of urea and acetamide. The rainbow trout were immersed in an aqueous solution of the BSA and the urea or acetamide for a period of 3 minutes and then were sacrificed. As shown in FIG. 3, BSA uptake increased significantly with increasing membrane permeability altering agent concentration up to a concentration of about 10%.

EXAMPLE X

To demonstrate the effectiveness of a membrane permeability altering agent pretreatment in rendering the membrane permeable to BSA, rainbow trout were immersed in a 5.3% aqueous NaCl solution for a period of 2 minutes, followed by immersion in a 2% BSA solution for a period of time up to 3 minutes. As shown in FIG. 4, a relatively high BSA serum level in the blood of the rainbow trout is attained within 120 seconds after immersion in the BSA solution.

EXAMPLE XI

The causative organism of Hagerman Redmouth Disease (ERMD), which causes serious mortality losses in salmonids, is a gram-negative bacterium. A proper classification of the organism has not been determined. Previous attempts to vaccinate fish against this disease by oral ingestion have been unsuccessful.

A confirmed culture of virulent ERMD organisms is propagated in a nutrient broth to a final organism count greater than $1 \times 10^{10}/0.1$ ml and then killed with 0.3% formaldehyde. Immunizing dosages of the ERMD bacterin are then delivered to rainbow trout in association with the membrane permeability altering agents and treatments listed in Table V.

TABLE V

Systemic Uptake of ERMD Bacterin By Rainbow Trout

| Test | Membrane Permeability Altering Agent | Treatment |
|---|---|---|
| 1 | Urea, 10g/100ml | 3 cycles of vacuum infiltration to about 1/5atm. with sharp vacuum break |
| 2 | Acetamide, 10g/100ml | 3 cycles of vacuum infiltration as in Test 1 |
| 3 | NaCl, 5g/100ml | 3 cycles of vacuum infiltration as in Test 1 |
| 4 | Urea, 10g/100ml | 10 min. immersion in Urea and ERMD |
| 5 | Acetamide, 10g/100ml | 10 min. immersion in Acetamide and ERMD |
| 6 | NaCl, 5g/100ml | 10 min. immersion in NaCl and ERMD |
| 7 | Urea, 10g/100ml | 10 min. immersion pretreatment in Urea followed by 3 min. in ERMD |
| 8 | Acetamide, 10g/100ml | 10 min. immersion pretreatment in Acetamide followed by 3 min. in ERMD |
| 9 | NaCl, 5g/100ml | 10 min. immersion pretreatment in NaCl followed by 3 min. in ERMD |

All of the systems listed in Table V successfully deliver immunizing doses of the ERMD bacterin to the trout. Simultaneous topical application of the membrane permeability altering agent and the ERMD bacterin has little, if any, adverse effect on the ERMD bacterin since its immunogenic potentcy is not lowered. The degree of protection in all cases is greater than 75%, and in some cases about 90%, against a 30 day post vaccination virulent challenge which produces 75% lethality in control samples.

EXAMPLE XII

Infectious Hematopoietic Necrosis (IHN) is a serious disease of anadromous salmonids, particularly chinook and sockeye salmon and rainbow trout. A formaldehyde killed, cell-free, filtered fluid vaccine was prepared from IHN virus cultured on a fathead minnow cell to a final titer of about $1 \times 10^{11}/0.1$ ml.

In the following tests, 60 rainbow trout juveniles per test, were contacted with the IHN vaccine by immersion in the vaccine fluid with and without urea and with and without vacuum infiltration, for a period of 5 minutes. When present in the vaccine medium, urea concentration was 10 g/100 ml. When used, vacuum infiltration employed 2 cycles to 1/5 atmosphere followed by rapid return to 1 atmosphere, all within a 3 minute period. The effectiveness of the above vaccination procedures against an intramuscular virulent challenge 45 days after vaccination is shown in Table VI.

TABLE VI

| Test | Vaccine | Vacuum Infiltration | Urea, 10g/100ml | Lethality with Virulent Challenge |
|---|---|---|---|---|
| 1 | None | No | No | 60 dead/60 population |
| 2 | None | No | No | 1/60 (no challenge) |
| 3 | IHN | No | No | 56/60 |
| 4 | IHN | Yes | No | 15/60 |
| 5 | IHN | No | Yes | 21/60 |
| 6 | IHN | Yes | Yes | 6/60 |

As shown in Table VI, simple immersion of the trout in the vaccine fluid showed no significant increase in immunity to the virulent challenge over that of the control group which received no treatment. The presence of the membrane permeability altering agent urea alone (Test 5) and the use of vacuum infiltration alone (Test 4) resulted in greatly enhanced immunity. The use of vacuum infiltration plus the presence of urea (Test 6) resulted in a very low lethality rate of 6 fish dead out of a population of 60. Some of these deaths could have resulted from a traumatic reaction to the intramuscular virulent challenge injection.

EXAMPLE XIII

The serious disease Vibrio generally hits fish of the salmon and trout species as they first enter the marine environment. A bacterium, *Vibrio anguillarum,* is the causative agent. A culture of Vibrio anguillarum is propagated in Difco Tryptic Soy Broth using a laboratory fermentor. When the organism cell count reaches about $2.5 \times 10^8/0.1$ ml, the culture is killed with 0.3% formaldehyde. Culture purity is confirmed by microscopic examination and by the rapid slide agglutination method using specific antiserum. The *Vibrio anguillarum* bacterin is then topically administered to coho salmon, as in Example XI, using the membrane permeability altering agents and treatments listed in Table V. Similar results are obtained.

EXAMPLE XIV

Coho salmon are immersed in an aqueous solution containing an effective dosage of the killed, washed, whole-celled preparation of Vibrio bacterin vaccine of Example XIII and the components of Table VII for a period of 10 minutes. After 30 days the salmon are subjected to a virulent Vibrio challenge. The effectiveness of the vaccination is shown in Table VII.

TABLE VII

| Test | Membrane Permeability Altering Agent | Mortality Rate After Virulent Challenge |
|---|---|---|
| 1 | None | 75% |
| 2 | Urea, 10gm/100ml | 21% |
| 3 | Urea, 10gm/100ml plus 30ppm 2-(4-thiazolyl) benzimidozole | 8% |

The decreased mortality rate in Test 3 can be attributed to enhanced uptake of the Vibrio bacterin by the salmon in the presence of both the membrane permeability altering agent and the vasodilator, 2-(4-thiazolyl) benzimidazole.

EXAMPLE XV

Ichthyopthiriasis, white spot disease or "Ich", is a serious disease in hatchery and aquarium held fishes and is caused by a large, parasitic external protozoan. The problem is difficult to control and more difficult to eradicate since the parasite contaminates the water environment and is generally protected by an overcovering of mucous which shields the organism from topically applied therapeutants. Nifurpirinol has been proposed as a treatment.

A population of small carp which are heavily spotted with the Ich infection, as confirmed by microscopic examination of wet smears, are divided into lots A and B. Lot A is treated by immersion for 5 minutes in an aqueous solution at 20° C. containing 7.0 ppm nifurpirinol plus 5 gm/100 ml of urea and 5.4 gm/100 ml of NaCl. Lot B is allowed to swim freely for 15 minutes in a 7.0 ppm solution of nifurpironol dissolved in 20° C. clean aquarium water. Fish of both lots are removed to clean aquariums and observed over a period of two weeks. Only the fish of lot A, those treated with nifurpirinol plus a membrane permeability altering agent, are seen to be virtually free of the Ich parasite. The Ich on fish of lot B are not visibly affected by the treatment.

EXAMPLE XVI

Various membrane permeability altering agents having molecular weights in the range of 58–61 were tested to determine their toxicity on young coho (silver) salmon. The salmon were immersed in aqueous solutions containing 5 g/100 ml of the membrane permeability altering agents. The results are listed in Table VIII.

TABLE VIII

Properties of Various Potential Membrane Permeability Altering Agents

| Agent | Mol. Wt. | Availability | Fish Toxicity | Other Properties |
|---|---|---|---|---|
| Acetaldoxime | 59.07 | Poor | Unknown | Expensive |
| Acetone | 58.08 | Excellent | toxic | Volatile and flammable |
| Allyl alcohol | 58.08 | Fair | Very toxic | Toxic to mammals |
| Propanol | 60.1 | Good | Moderately toxic | Toxic to mammals |
| Isopropanol | 60.1 | Excellent | Delayed toxicity | Toxic to mammals |
| Ethylene diamine | 60.1 | Good | Very toxic | |
| Sodium chloride | 58.45 | Excellent | Low toxicity | Chemically stable and normally found in water-living animals |
| Acetamide | 59.07 | Excellent | Non-toxic | |
| Urea | 61.08 | Excellent | Non-toxic | |
| 2 - Aminoethanol | 61.08 | Poor | Toxic | Expensive |

From the above properties, NaCl, acetamide and urea can be seen to be the most desirable membrane permeability altering agents for use in practice.

EXAMPLE XVII

Rainbow trout were divided into two lots, lot A and lot B. The fish of lot A were immersed for a period of 5 minutes in an aqueous solution containing 10 g/100 ml of urea and *Vibrio anguillarum* bacterin diluted to a standard titer of $1 \times 10^9/0.1$ ml with saline water. The fish of lot B were immersed for a period of 5 minutes in an aqueous solution identical to that of lot A with added 55 micrograms/ml DEAE dextran and 300 micrograms/ml of KOH neutralized Carbopol 934 (a carboxyvinyl polymer). On the 46th day after vaccination, the fish of both lots A and B were subjected to a virulent *Vibrio anguillarum* bacterial challenge. The effectiveness of the vaccination is shown in Table IX.

TABLE IX

| Lot | Viscosity of Vaccinating Media (cp) | Survival Rate After Virulent Challenge |
|---|---|---|
| Control | 1.0 | 30% |
| A | 2.5 | 80% |
| B | 13.0 | 50% |

The dextran and carbovinyl polymer had no effect on the potency of the Vibrio bacterin. The higher mortality rate realized in lot B is attributed to a lesser degree of systemic uptake of the Vibrio antigen by the fish from the higher viscosity solution. Since a survival rate of less than 50% would generally be unacceptable in large scale vaccination programs, the viscosity of the health-modifying agent delivery medium is preferably maintained at a relatively low level.

It can be seen by reference to Examples V and VI that equivalent concentrations of the preferred membrane permeability altering agents, as described herein, facilitate a higher degree of systemic uptake of health modifying agents by water-living animals than does DMSO. Further, it has been shown in Examples II, XI, XII and XIII that the preferred membrane permeability altering agents may be used in conjunction with one or more vacuum-vacuum break cycles to achieve the desired result. The correlation of membrane permeability with hyperosmotic solute molecular weight is independent of the delivery system, i.e., rendering the epithelial membrane reversibly permeable by contact with a membrane permeability altering agent alone, or rendering the membrane reversibly permeable by contact with a membrane permeability altering agent coupled with vacuum infiltration.

While I have discovered that certain membrane altering agents having particular molecular weight characteristics produce surprising and unexpected results, I do not know the reason why these specific agents produce such results.

While inventive concepts have been herein disclosed in reference to presently preferred and illustrative embodiments of the invention, it is contemplated that these concepts may be variously otherwise employed in alternate systems for the delivery of health modifying agents to water-living animals. It is intended that the appended claims be construed to cover alternate embodiments of the inventive concepts except insofar as precluded by the prior art.

What is claimed is:

1. A method of enhancing the penetration into and across an epithelial membrane barrier of a water-living animal of a health modifying agent capable of eliciting a desired health modifying effect therefrom comprising contacting the water-living animal with a sufficient amount of an aqueous solution or dispersion of the health modifying agent to produce the desired health modifying effect on the water-living animal and a solution comprising a sufficient concentration of a second agent selected from the group consisting of acetamide, urea, sodium chloride and mixtures thereof to enhance penetration and systemic uptake of the health modifying agent to achieve the desired health modifying effect.

2. The method of claim 1 wherein the solution comprising the second agent comprises a hyperosmotic concentration of the second agent.

3. A method of treating water-living animals to impart a health modifying agent thereto, comprising contacting water-living animals with a solution comprising a hyperosmotic concentration of a second agent selected from the group consisting of acetamide, urea, sodium chloride and mixtures thereof, and contacting the water-living animals with a health modifying agent for a sufficient period of time for the water-living animals to absorb said health modifying agent.

4. The method of claims 2 or 3 wherein the water-living animal is contacted with the health modifying agent in a soluble or colloidally dispersed mixture comprising the health modifying agent and the second agent.

5. The method of claim 4 wherein the mixture is contacted with the water-living animal for a period of about 3 to about 10 minutes or more.

6. The method of claims 2 or 3 wherein the water-living animal is contacted with the second agent prior to contacting the membrane with the health modifying agent.

7. The method of claim 6 wherein the water-living animal is contacted with the second agent for a period of about 3 to about 10 minutes and then contacted with the health modifying agent for a period of about 2 to about 5 minutes.

8. The method of claims 2 or 3 wherein the concentration of the second agent is at least about 3 times its isosmotic concentration.

9. The method of claims 2 or 3 wherein the second agent comprises a 1 mol:1 mol ratio aqueous mixture of acetamide to sodium chloride.

10. The method of claims 2 or 3 wherein the membrane permeability altering agent comprises a 1 mol:2 mol ratio aqueous mixture of urea to sodium chloride.

11. The method of claims 2 or 3 which further comprises purifying the second agent prior to contacting the water-living animal with the second agent by passing the second agent through a bed of activated charcoal.

12. The method of claims 2 or 3 wherein the second agent further comprises an amount of 2-(4-thiazolyl) benzimidazole effective to enhance said method.

13. The method of claims 2 or 3 wherein the water-living animal is contacted with the second agent by immersing the animal in the aqueous solution of the second agent.

14. The method of claims 2 or 3 wherein the water-living animal is contacted with the health modifying agent by immersing the animal in an aqueous solution or dispersion of the health modifying agent.

15. The method of claims 2 or 3 wherein the water-living animal is contacted with the second agent while the animal is either partially or totally out of water.

16. The method of claims 2 or 3 wherein the water-living animal is contacted with the health modifying agent while the animal is either partially or totally out of water.

17. The method of claims 2 or 3 wherein the aqueous solution or dispersion of the health modifying agent has a viscosity less than about 10 cp.

18. The method of claims 2 or 3 wherein the water-living animals are fish.

19. The method of claims 2 or 3 wherein the health modifying agent is an antigen.

20. The method of claims 2 or 3 wherein the health modifying agent is a chemotherapeutant.

21. The method of claim 19 wherein the antigen is infectious hematopoietic necrosis.

22. The method of claim 19 wherein the antigen is Vibrio anguillarum bacterin.

23. The method of claim 19 wherein the antigen is Aeromonas salmonicida bacterin.

24. The method of claim 19 wherein the antigen is Bovine serum albumin vaccine.

25. The method of claim 19 wherein the antigen is Enteric Redmouth bacterin.

26. The method of claim 19 wherein the antigen is Infectious pancreatic necrosis.

27. A method of treating water-living animals comprising immersing said animals in a solution comprising a hyperosmotic concentration of an agent selected from the group consisting of acetamide, urea, sodium chloride and mixtures thereof, and further comprising a health modifying agent in a sufficient amount to be taken up by said animals.

28. A method of improving the health and/or welfare of water living animals comprising treating said animals with a solution comprising a hyperosmotic concentration of an agent selected from the group consisting of acetamide, urea, sodium chloride and mixtures thereof and further comprising a health and/or welfare enhancing agent in a sufficient amount to be taken up by said animals.

* * * * *